United States Patent [19]

Pletcher

[11] 4,371,337

[45] Feb. 1, 1983

[54] ORTHODONTIC BRACKET

[76] Inventor: Erwin C. Pletcher, P.O. Box 566, Rancho Santa Fe, Calif. 92067

[21] Appl. No.: 265,377

[22] Filed: May 20, 1981

[51] Int. Cl.³ .............................................. A61C 7/00
[52] U.S. Cl. ..................................................... 433/10
[58] Field of Search ....................... 433/10, 13, 17, 11

[56] References Cited

U.S. PATENT DOCUMENTS 1,764,067   6/1930   Craigo .................................... 433/20
4,268,249   5/1981   Fostee .................................... 433/10

Primary Examiner—Robert Peshock
Attorney, Agent, or Firm—Christie, Parker & Hale

[57] ABSTRACT

An orthodontic bracket assembly with a rotatable locking member anchored to a base by a slotted bar configured to receive an arch wire. The bar is initially rotatable with respect to the base, and is then fixed in a position providing any torque angulation which may be needed for tooth alignment. The locking member rotates on the bar to capture the arch wire in the bracket assembly.

14 Claims, 11 Drawing Figures

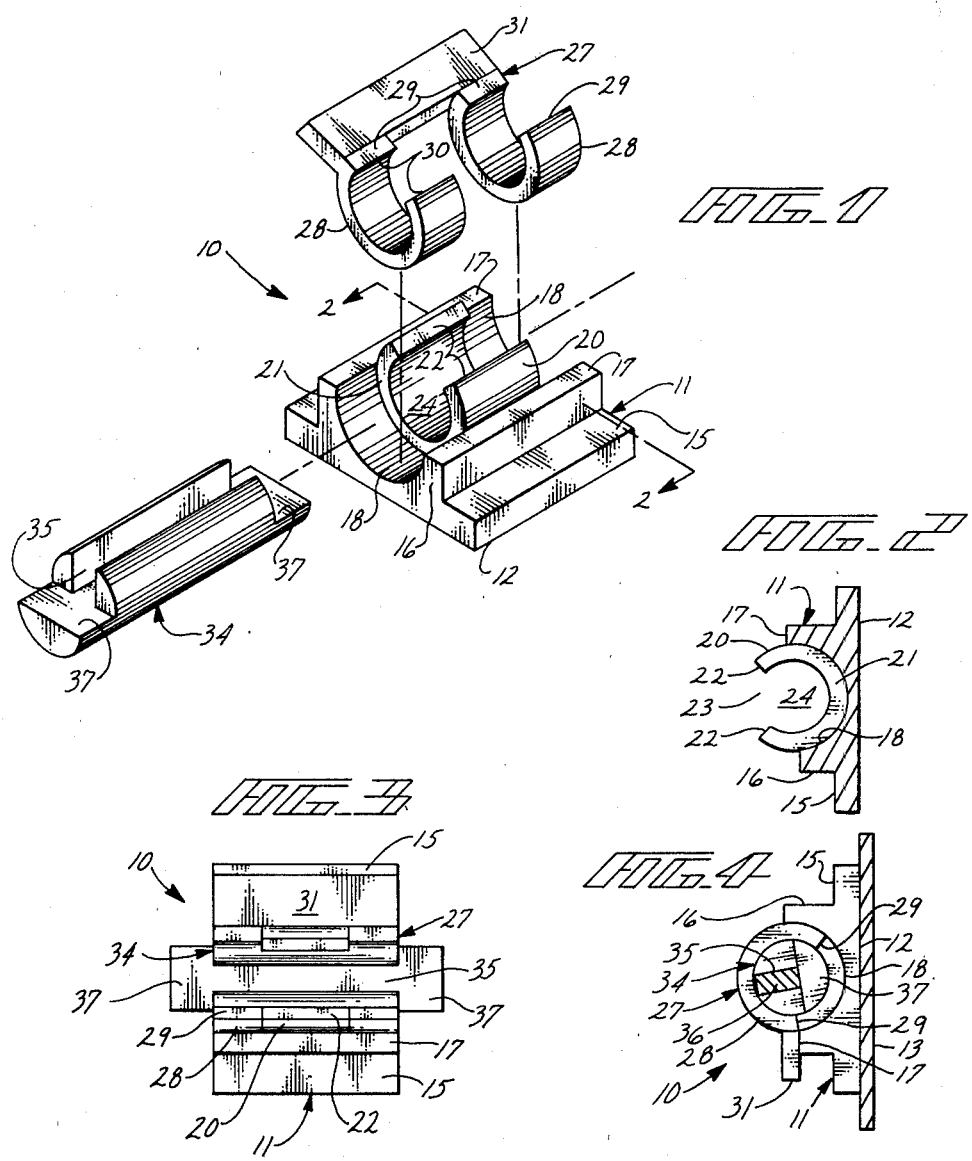

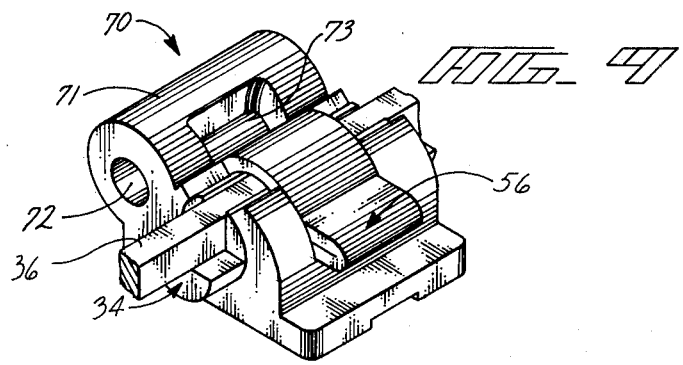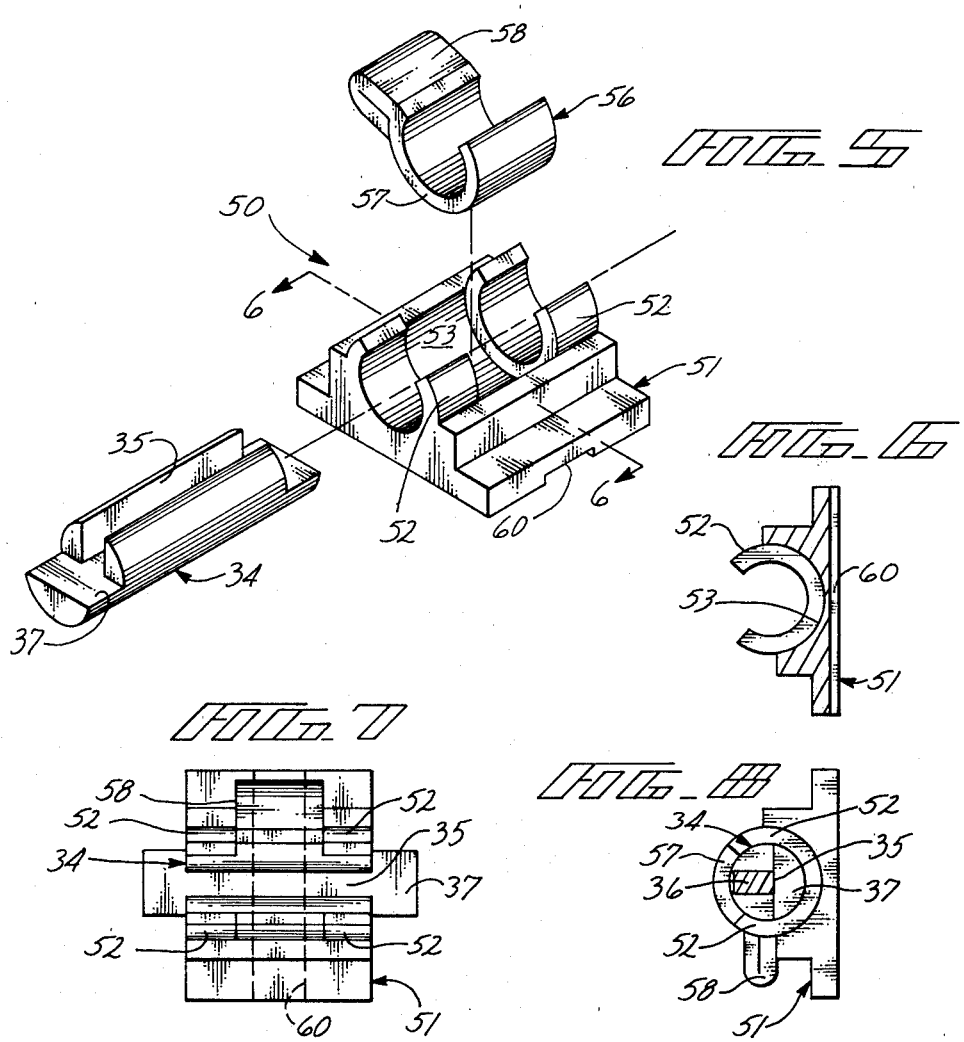

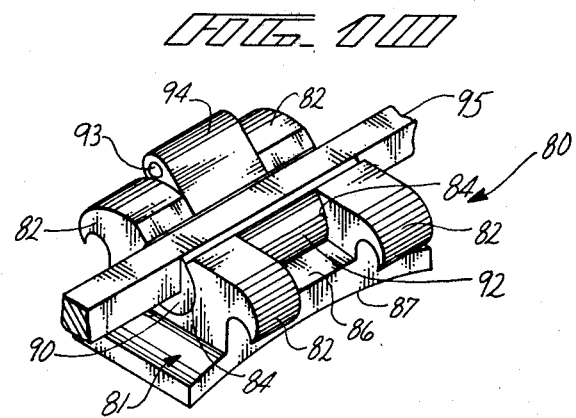
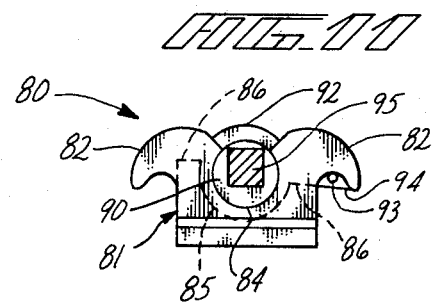

4,371,337

ORTHODONTIC BRACKET

BACKGROUND OF THE INVENTION

My U.S. Pat. No. 4,077,126 (the disclosure of which is incorporated herein by reference) shows an orthodontic bracket with a rotatable locking member mounted within a body portion of the bracket. Reference is made to my earlier patent for a discussion of the function of an orthodontic bracket, and the problems inherent in using conventional brackets which require installation of tie or ligature wires to secure an arch wire to the bracket.

The new bracket herein disclosed is an improvement on the locking bracket described in the aforementioned patent. The new assembly is typically of three piece construction, including a base, an open-slotted bar adapted for attachment to the base, and a locking member which is rotatably mounted on the bar. The locking member is preferably captured between supporting bearing surfaces on the base and bar, and the bar can be positioned during assembly to provide a corrective torque force to the tooth on which the bracket is to be mounted.

The rotatable locking member eliminates need for ligature wires at most or all stages of orthodontic treatment, but provision is made for use of ligatures if the tooth is so severely malpositioned that seating of the arch wire in the bracket cannot be achieved during early treatment. When reasonable tooth alignment is present, ligatures are eliminated, and the arch wire is installed and exchanged between treatment phases simply by rotating the locking members of the affected brackets to an open position.

SUMMARY OF THE INVENTION

This invention relates to a ligature-free orthodontic bracket with a rotatable locking member movable between open and closed positions to receive and capture an orthodontic arch wire. The bracket is preferably of three-piece construction, and includes a base, a locking member, and an arch-wire bar.

The locking member has a hollow part-circle hub positionable on the base adjacent a forwardly extending part-circle support member on the base. The hub and support member have aligned passages which are preferably cylindrical, and the bar makes a slip fit within these passages. When so assembled, the bar is then rigidly secured to the base (with torque angulation of an arch-wire slot in the bar if desired), thereby capturing the locking member on the base and providing an axle-like rotational support for the locking member.

The hub and support member define clearance slots which are aligned with the arch-wire slot when the locking member is in the open position. After the arch wire is installed, the locking member is rotated to the closed position to capture the arch wire within the bar.

DESCRIPTION OF THE DRAWINGS

FIG. 1 is an exploded pictorial view of an orthodontic bracket according to the invention;

FIG. 2 is a sectional view of a bracket base on line 2—2 of FIG. 1;

FIG. 3 is a front view of the bracket assembly with a rotatable locking member in an open position;

FIG. 4 is an end view of the bracket assembly with the locking member closed, and showing an arch-wire bar positioned for application of torque to a tooth;

FIG. 5 is an exploded perspective view of an alternative bracket according to the invention;

FIG. 6 is a sectional view on line 6—6 of FIG. 5 and showing a bracket base used in the assembly;

FIG. 7 is a front view of the bracket assembly shown in FIG. 5 with a rotatable locking member in an open position;

FIG. 8 is an end view of the bracket assembly shown in FIG. 5;

FIG. 9 is a pictorial view of a bracket of the general style shown in FIGS. 5–8, but with the addition of a buccal tube;

FIG. 10 is a pictorial view of another style of bracket incorporating the invention; and FIG. 11 is an end view of the bracket shown in FIG. 10.

DESCRIPTION OF THE PREFERRED EMBODIMENTS

FIGS. 1–4 show a first embodiment of an orthodontic bracket assembly 10 according to the invention. The assembly includes a bracket base 11 having a lingual or rear face 12 adapted for attachment to a tooth. The bracket base may be welded to a conventional tooth band 13 (FIG. 4) configured for cemented attachment to the tooth, or alternatively the base can be provided with a mesh or other conventional base configuration for direct cement attachment to the tooth.

Projecting from a labial (this term also being used herein to include the buccal direction) or front face 15 of the bracket base is a boss or support member 16 having vertically spaced front walls 17 connected by half-cylindrical concave bearing surfaces 18 at opposite ends of the bracket base. Integrally formed in the central portion of this recessed saddle-like cradle or bearing surface is a partial ring 20 having opposed end surfaces 21. The tops of the ring extend forwardly and inwardly from front faces 15 to terminate in end walls 22 between which is defined an entrance or slot 23 communicating with the hollow interior of the ring.

The inner surface of partial ring 20 defines a cylindrical bore or opening 24 which is coaxial with adjacent bearing surfaces 18. Opening 24, however, has a smaller radius than that of the bearing surfaces, the junction between the zones being defined by end surfaces 21. Bearing surfaces 18 have a perimeter which extends around approximately 180 degrees, whereas the perimeter of opening 24 extends around approximately 270 degrees, the remaining 90 degrees being open to define slot 23. Walls 22 extend radially at the opposed ends of the ring, forming a chamfered entrance to slot 23.

A locking member 27 has a hub formed by a pair of coaxial and axially spaced partial rings 28, the periphery of each ring extending around more than 180 degrees, but equal to or less than the circumferential extent of ring 20 on the bracket base. The outside diameter of each ring 28 corresponds to the inside diameter of bearing surfaces 18 on the base, and the inside diameter of rings 28 corresponds to the inside diameter of partial ring 20 on the base.

Rings 28 terminate in radially extending end walls 29 forming a chamfered entrance to a second slot 30 in communication with the cylindrical inner surface of the rings. The axial or mesiodistal dimension of the rings corresponds to that of bearing surfaces 18 such that the rings nest on the bearing surfaces and make a slip fit on opposite sides of partial ring 20 on the base. Rings 28 are joined by an integrally formed and radially extending tab or handle 31.

A generally cylindrical arch-wire bar 34 has an outside diameter selected to make a slip fit within the cylindrical inner surfaces of rings 20 and 28. A forwardly open arch-wire slot 35 extends along the length of the bar, and is configured to receive an edgewise arch wire 36 (FIG. 4) of the usual rectangular cross section. The dimensions of the arch-wire slot can of course be varied to accommodate arch wires of different sizes and cross sections.

Bendable tabs 37 extend from opposite ends of the bar at the base of the arch-wire slot. Preferably, the mesiodistal length of the slotted portion of the arch-wire bar corresponds to the mesiodistal dimension of bracket base 11, and tabs 37 overhang the base.

To assembly the bracket, locking member 27 is positioned against the front surface of the bracket base with the outer surfaces of rings 28 resting on concave bearing surfaces 18 so the inner surfaces of rings 28 are coaxial with ring 20. Arch-wire bar 34 is then slipped mesiodistally or sideways into the openings through rings 20 and 28. The locking member is thus made captive on the base by these rings which extend more than 180 degrees, but the locking member is free to rotate between open and closed positions on the axle-like end portions of the bar.

With the parts so assembled, arch-wire bar 34 is rotated to a position in which the base of the arch-wire slot is parallel to the rear face of the bracket base if no torque is to be introduced into the bracket assembly. Alternatively, any desired degree of torgue angulation of the arch-wire slot can be provided by rotating the bar to a selected position as suggested in FIG. 4. When the position of the bar has been determined, the bar is rigidly secured to ring 20 of the base. This fastening means is most conveniently provided by conventional brazing, welding or soldering.

The assembled bracket is shown in FIG. 3 with the arch-wire slot in a zero-torque position, and the locking member fully open with handle 31 abutting one of front walls 17 on the bracket base. In this position, all slots in the bracket assembly are aligned, the first slot being the entrance to partial ring 20, the second slot being the entrance to rings 28, and the third slot being the arch-wire slot itself.

An arch wire is then fitted in slot 35 of the arch-wire bar, and the locking member is rotated to a closed position as shown in FIG. 4 (showing torque angulation of the arch-wire slot) with handle 31 abutting the other of front walls 17 of the bracket base. Rotation of the locking member to this position closes the entrance slots to rings 20 and 28, making the arch wire labiolingually captive within the bracket, while still permitting axial movement of the arch wire with respect to the bracket as is desirable in many orthodontic treatment phases. The first and second slots are significantly wider than the arch-wire slot to permit installation of the arch wire when the bar is rotated to a torque-angulation position.

Tabs 37 on oposite ends of the arch-wire bar are useful in several ways. First, in some forms of treatment, it may be desirable to bend these tabs slightly forwardly or labially to be urged against the rear or lingual surface of the arch wire. Secondly, should it be necessary to use a ligature wire during some preliminary phase of treatment, the tabs can be bent slightly rearwardly to provide a pair of tie wings around which the ligature can be secured.

Another embodiment of the invention is shown in FIGS. 5-8 which illustrate a bracket assembly 50 using a single-ring centrally positioned locking member in contrast to the dual-ring locking member used in assembly 10. A bracket base 51 of assembly 50 is generally similar to base 11 previously described, with the exception that partial ring 20 in the earlier embodiment is replaced by a pair of mesiodistally spaced partial rings 52 at opposite ends of the base. A recessed enlarged-diameter concave bearing surface 53 is disposed between rings 52, and surface 53 is coaxial with the cylindrical inner surfaces of rings 52.

A locking member 56 for assembly 50 has a hub formed as a partial ring 57 with an outside diameter corresponding to the curvature of bearing surface 53. The axial dimension of ring 57 is selected so the ring makes a slip fit between partial rings 52 on the bracket base. A tab or handle 58 extends radially from one end of ring 57. Locking member 56 can be cast or machined, but is shown in the drawings as a stamped member formed from sheet metal, and with handle 58 in a folded and doubled-back configuration.

Arch-wire bar 34 as previously described is also useful in assembly 50, and is fitted through the inner bores or passages of rings 52 and 57 to capture the locking member on the base, and to serve as a axle or bearing surface for the locking member. As previously described, the arch-wire bar is rotated to any desired degree of torque angulation, and the bar is then secured in place by welding, brazing, soldering, staking, cementing, or the like. It may be advantageous to make the locking member of a non-solderable or non-brazable material to avoid any bonding of this part to the other components of the bracket. If desired, a vertically extending slot 60 may be formed in the rear or lingual face of bracket base 51 to receive auxilliary attachments, or to provide another anchorage for a ligature wire should ligation be necessary in a preliminary treatment stage.

FIG. 9 shows a slightly modified bracket assembly 70 which generally conforms to the bracket shown in FIG. 5-8, with the exception that a buccal tube 71 has been added to the bracket base which is shown as a cast component with more rounded contours as compared to base 51 described above. Assembly 70 thus provides a convertible buccal molar tube and edgewise bracket useful during both early and later stages of orthodontic treatment. Buccal tube 71 is integrally formed with the base of the bracket assembly, and has a cylindrical passage 72 therethrough to receive, for example, the end of a face-bow appliance. As shown in FIG. 9, the front face of the buccal tube defines a recess 73 which receives the handle of the locking member when the locking member is in an open position.

FIGS. 10 and 11 show yet another embodiment of the invention in the form of a twin edgewise bracket 80 assembly having a base 81. The bracket base is generally similar to base 51 described above, but is provided with conventional lingually extending tie wings 82 around which a ligature wire can be tied in situations where the arch wire cannot be properly seated in the bracket during an initial stage of treatment. The tie wings may also be useful in anchoring springs or other auxiliary appliances.

Base 81 includes a pair of mesiodistally spaced partial rings 84 which are integrally formed with the respective tie wings, and a recessed enlarged-diameter concave bearing surface 85 extends between the rings just as in base 51. Labially extending walls 86 on the base provide stops for the locking member (described below) in the open and closed positions. A lingual face 87 of the base may be concave about an occlusogingival axis as is conventional in this style of bracket.

Bracket assembly 80 also includes an arch-wire bar 90 which is similar to bar 34 previously described, with the exception that bendable tabs 37 are eliminated in view of the provision of tie wings on the bracket base. The assembly is completed by a locking member 92 which is similar to member 56 with the optional addition of a small projecting button or detent 93 on the side surface of the end of a locking-member handle 94.

FIG. 10 shows assembly 80 with the locking member open, and an arch wire 95 received in the slot of the arch-wire bar. The locking member is in the closed position in FIG. 11, with detent 93 nested beneath associated tie wing 82. The detent is forced past the inner side surface of adjacent partial ring 84 to snap into a closed position. Other forms of detent or similar locking means can be provided if additional locking security is felt necessary. As shown in the drawings, walls 86 on the base may be of different heights to position the locking member properly in the open and closed positions.

The various components of the brackets described above may be machined from grades of stainless steel conventionally used in orthodontic appliances, or may alternatively be cast in either metal or plastic. The locking member and arch-wire bar can also be stamped to shape using conventional techniques. Assembly of the three components is quick and straightforward, and the design is especially advantageous in that any desired degree of torque may be introduced prior to rigid attachment of the arch-wire bar to the bracket base. If desired, some form of torque-position detent indexing may be provided (e.g., mating teeth or ribs on the arch-wire bar and support member), bit it is believed that the desired angulation can be easily established during assembly without this feature.

When the arch-wire bar is secured in place, the locking member is permanently captive within the bracket assembly, and cannot be misplaced prior to installation of the bracket on a tooth or tooth band. The locking member is especially well supported in these designs in that the inside diameter of the locking member makes a rotational slip fit on the arch-wire bar, and the outside diameter of the locking member rests in the cradle-like surface of the bracket base adjacent the partial ring or rings on the base.

While the arch-wire bar has been illustrated as being mesiodistally coextensive with the bracket base, it is contemplated that some treatment programs may be enhanced by using a larger bar which overhangs the sides of the base or the bar-supporting rings. The length of the bar can be selected to suit the requirements of a specific application, and longer bars are entirely useful when an extended seat for the arch wire is needed.

Directional terminology used herein such as labial and lingual is intended to apply to the bracket as conventionally mounted on a labial or outer face of a tooth. The bracket, however, is useful for attachment on the lingual or inner tooth face, and it is to be understood that appropriate adjustments is terminology are necessary in such lingual-appliance treatment programs. It is sometimes desirable to provide a vertical arch-wire slot in a lingual appliance, and this configuration is easily achieved by rotating the bracket to position the slot as needed, and by conventionally contouring the bracket base to compensate for this orientation.

There has been described an orthodontic bracket which eliminates the need for ligature wires in most or all phases of conventional orthodontic treatment. The bracket is physiologically clean, and is configured to enable economical and rapid manufacture and assembly. The new designs are felt to be advantageous to both orthodontists and manufacturers of orthodontic appliances in that they have been designed with the manufacturing process in mind, without any sacrifice in flexibility and usefulness to the orthodontist.

What is claimed is:

1. An orthodontic bracket assembly, comprising:
    a base with a labially extending support member having a mesiodistally extending opening therethrough, the opening extending through a first slot in the support member to provide clearance for insertion of an arch wire;
    a locking member having a hub with a mesiodistal passage therethrough, the passage extending through a second slot to provide clearance for insertion of the arch wire; and
    an arch-wire bar configured to fit in the support-member opening and locking-member passage, the bar having a mesiodistal third slot to receive the arch wire, the locking member being rotatable on and captively retained by the bar, the first and third slots being generally aligned;
    the locking member being rotatable between open and closed positions, the open position aligning the slots to enable seating of an arch wire in the bar slot, and the closed position placing the second slot out of alignment with the first and third slots to capture the arch wire within the bracket assembly.

2. The assembly defined in claim 1 wherein the first slot is wider than the third slot, and the bar is adjustable in position on the base to provide a selected amount of torque angulation of the third slot, and further comprising means for securing the bar to the base in the selected torque angulation.

3. The assembly defined in claim 1 wherein the support member opening and locking-member passage are generally cylindrical, and the arch-wire bar is generally cylindrical to make a slip fit within said opening and passage.

4. The assembly defined in claim 3 wherein the circumferences of said opening and passage extend more than 180° to the associated first and second slots.

5. The assembly defined in claim 4 wherein the support member defines a partial ring extending labially from the base, and the locking-member hub defines a pair of mesiodistally spaced partial rings configured to fit on opposite sides of the support-member partial ring, the base having concave surfaces on opposite sides of the support member to receive and support the hub rings.

6. The assembly defined in claim 4 wherein the support member defines a pair of mesiodistally spaced partial rings extending labially from the base, and the locking member hub defines a partial ring configured to fit between the support-member rings, the base having a labial concave surface between the support-member rings to receive and support the hub ring.

7. The assembly defined in claims 5 or 6 wherein the arch-wire bar is adjustable in position on the base to provide a selected amount of torque angulation of the third slot, and further comprising means for securing the bar, to the base in the selected torque angulation.

8. The assembly defined in claim 7 wherein the locking member includes a radially extending handle.

9. The assembly defined in claim 7 wherein opposite ends of the arch-wire bar have tabs extending therefrom.

10. The assembly defined in claim 9 wherein said tabs are bendable.

11. The assembly defined in claim 7, and further comprising a buccal tube on the base.

12. The assembly defined in claim 7 wherein the base has a rear face with a vertically extending recessed slot.

13. An orthodontic bracket assembly, comprising:
a base having a support member;
a locking member positioned against the base adjacent the support member;
the support and locking members having coaxial and mesiodistally extending aligned passages therethrough;
an arch-wire bar having a open slot to receive an arch wire, the bar being configured to make a slip fit into said aligned passages and thereby to make the locking member captive on the base, the locking member being rotatable on the bar between open and closed positions to open and close the arch-wire slot of the bar.

14. A three-piece orthodontic bracket assembly, comprising:
a base having a generally ring-shaped support member integrally formed therewith and extending forwardly therefrom; the member having an inner surface with a circumference extending more than 180 degrees but less than 360 degrees to a open first slot;
a locking member having a generally ring-shaped hollow hub with an inner-surface circumference extending more than 180 degrees but less than 360 degrees to a open second slot, the locking member hub being positioned on the base adjacent the support member; and
an arch-wire bar having a mesiodistally extending third slot therein to receive an arch wire, the bar being fitted within the support member and locking-member hub and secured to the support member to make the locking member rotatably captive on the base.

* * * * *